United States Patent [19]
Rohr

[11] 3,958,574
[45] May 25, 1976

[54] MASCULINE HYGIENE DEVICE
[76] Inventor: Joan M. Rohr, 71 Grotto Ave., Providence, R.I. 02906
[22] Filed: Sept. 30, 1974
[21] Appl. No.: 510,415

[52] U.S. Cl. .............................. 128/295; 210/455
[51] Int. Cl.² ............................................ A61F 5/44
[58] Field of Search ............... 128/275, 284, 290 R, 128/294, 295, 172; 210/463–468, 455, 470, 471; 15/209 R, 210 R

[56] References Cited
UNITED STATES PATENTS

| 87,932 | 3/1869 | Hoffman | 128/294 |
| 2,891,546 | 6/1959 | Galloway | 128/295 |
| 2,896,788 | 7/1959 | Hoffberger | 128/275 |
| 3,212,500 | 10/1965 | Bardy | 128/295 |
| 3,334,574 | 8/1967 | Douglas | 210/455 |
| 3,398,836 | 8/1968 | Hugentobler | 210/455 |
| 3,858,584 | 1/1975 | Johnson | 128/295 |

Primary Examiner—Robert W. Michell
Assistant Examiner—Henry S. Layton
Attorney, Agent, or Firm—Barlow & Barlow

[57] ABSTRACT

A cup of absorbent material of a size to cap the male organ for absorbing urine moisture after urination and provided with a tab or handle for manipulating the same.

2 Claims, 3 Drawing Figures

MASCULINE HYGIENE DEVICE

BACKGROUND OF THE INVENTION

After urination there is often left moisture on the end of the male penis which stains the underclothing or trousers and sometimes causes a mess about the water closet. There does not seem to be any hygienic device available for such a situation. Bandages such as shown in U.S. Pat. No. 731,201 have been provided for medical treatment or for other uses and are not intended for the use for which this invention is intended and are complicated and expensive. This invention is intended to clean up the urine moisture after urination and prevent the staining of the underclothing or trousers and assist in preventing messy conditions about the water closet.

SUMMARY OF THE INVENTION

A cup of absorbent material is provided of a size to receive the end of the male penis after urination to absorb the moisture of urine which may be left thereon. The cup may also have been pretreated with a medication of a deodorant nature and is also provided with a tab or handle for manipulating the cup. The cup is completely disposable as one unit for flushing in usual sanitary systems.

DESCRIPTION OF THE PREFERRED EMBODIMENT

Paper towels of an absorbent nature have long been used for blotting the hands after washing to remove the moisture therefrom, and it is this type of material of which the cup of this invention is formed.

Figure 1:
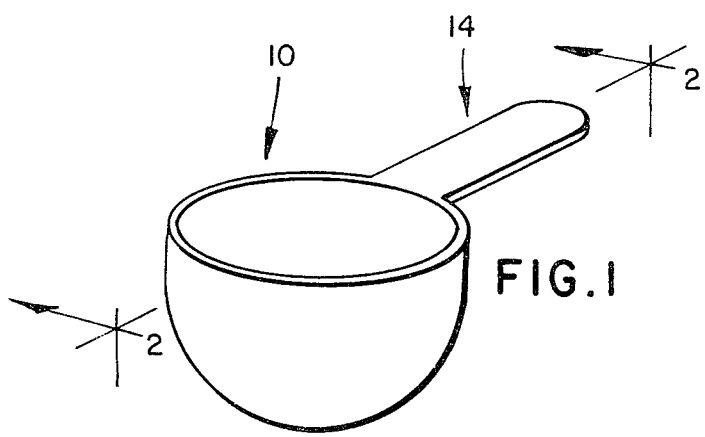
FIG. 1 is a perspective view of the cup of this invention with a handle shown thereon.
Figure 2:
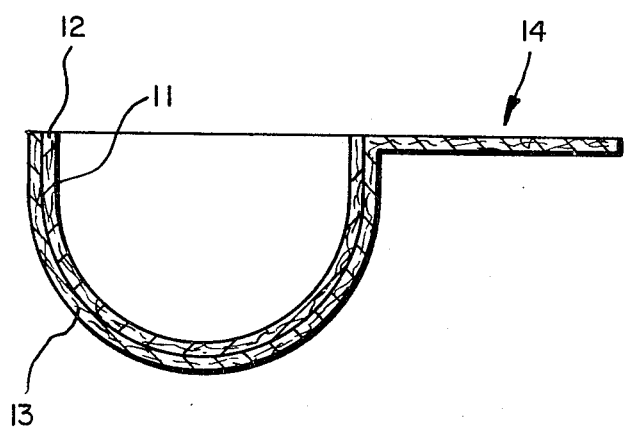
FIG. 2 is a sectional view through the handle showing several plies of paper of an absorbent nature.
Figure 3:
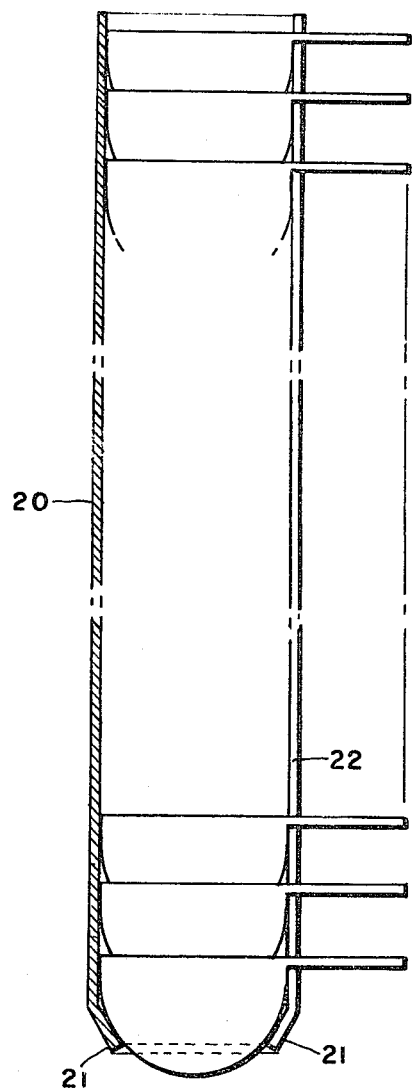
FIG. 3 is a sectional view of a dispenser for the cup.

With reference to the drawing, a cup 10 (shown in FIG. 1) is molded from an absorbent paper material in a shape such as shown and of a size to receive the end of the male penis. Preferably there would be three layers of paper 11, 12 and 13 although more or less may be utilized depending upon the weight of the paper which is used. These may be suitably molded or formed in the shape shown and in various sizes where it is found necessary.

The plies of paper may extend into a handle designated generally 14 and will consist of one or two or three layers of paper as may be found necessary. The handle will be of an extent capable of being grasped by the hand for manipulation of the cup. Preferably it will extend from the open edge of the cup and may be a continuation of the various plies of paper used in the cup. In some cases the handle may be separately formed and attached to the cup.

A device of this character may be dispensed from a tubular container 20 such as the drinking cups are dispensed from, which container may be handily used adjacent the water closet for use after each male urination and then flushed. Lips 21 at the lower edge of container 20 retain the cups in the container and sufficient flexibility between a cup and the container permit of the removal of a cup from the container by grasping the handle 14 which protrudes from the container through slot 22 of the container. Particularly, this device would be very useful in places where men handle or prepare food as they tend to be forgetful of washing hands after urinating. The device prevents any contact of the human hands with the penis. In the average home it would be placed beside the water closet and flushed down the same such as toilet paper, or in a men's washroom, in a small container.

I claim:

1. A one use masculine hygiene disposable device to be stored in a container adjacent the point of use comprising a self-supporting cup having an arcuate end wall and a continuous side wall and of a size to receive the end of the male penis, said cup having an open edge and an integral tab extending from the open edge of said cup, said tab being of a size to be grasped by the hand, said cup being completely of a material capable of absorbing urine moisture and said material being of a plurality of plies of an absorbent paper.

2. A device as in claim 1 wherein said cup contains medication of a deodorant nature.

* * * * *